US007634314B2

(12) United States Patent
Applebaum et al.

(10) Patent No.: US 7,634,314 B2
(45) Date of Patent: Dec. 15, 2009

(54) POWERED STIMULATION DEVICE

(75) Inventors: Robert Applebaum, Los Angeles, CA (US); Alejandro Covalin, Edina, MN (US); Philip Klein, Los Angeles, CA (US)

(73) Assignee: AK Beauty Enterprises, LLC, Beverly Hills, CA (US)

( * ) Notice: Subject to any disclaimer, the term of this patent is extended or adjusted under 35 U.S.C. 154(b) by 607 days.

(21) Appl. No.: 11/290,724

(22) Filed: Nov. 30, 2005

(65) Prior Publication Data

US 2007/0123807 A1 May 31, 2007

(51) Int. Cl.
*A61N 1/00* (2006.01)
*A61H 1/00* (2006.01)
*A61H 1/02* (2006.01)
*A61H 5/00* (2006.01)

(52) U.S. Cl. ........ 607/2; 601/20

(58) Field of Classification Search ........ 601/15, 601/19, 20; 607/1, 2
See application file for complete search history.

(56) References Cited

U.S. PATENT DOCUMENTS 1,103,669 A * 7/1914 Gibbs ........ 601/20
1,728,368 A * 9/1929 Saxer ........ 601/20
3,735,756 A 5/1973 Richards et al.
3,756,224 A * 9/1973 Laymon ........ 601/125
4,033,356 A 7/1977 Hara
4,124,030 A 11/1978 Roberts
4,813,404 A * 3/1989 Vallis ........ 601/125
5,005,561 A 4/1991 Nishikawa
5,067,478 A * 11/1991 Berlant ........ 601/15
5,513,651 A 5/1996 Cusimano et al.
5,575,760 A 11/1996 Masuda
5,711,758 A 1/1998 Tseng
5,797,966 A * 8/1998 Bontoux et al. ........ 607/3
6,126,620 A 10/2000 Graston
6,324,432 B1 11/2001 Rigaux et al.
7,083,581 B2 * 8/2006 Tsai ........ 601/15
2002/0143373 A1 * 10/2002 Courtnage et al. ........ 607/91
2005/0004508 A1 1/2005 Sun et al.

FOREIGN PATENT DOCUMENTS

GB 2 261 377 A 5/1993

OTHER PUBLICATIONS

PCT: International Search Report and Written Opinion of the International Searching Authority, dated Sep. 25, 2007.
Applebaum, Robert, "Consent to Be a Subject in the Non Invasive Body Contouring Study", 2004.
Applebaum, Robert, "Photographic Consent and Release—Body Sculpting and Cellulite Treatment Study", 2004.

* cited by examiner

*Primary Examiner*—Justine R Yu
*Assistant Examiner*—Kristen C Matter
(74) *Attorney, Agent, or Firm*—Jeffer Mangels Butler & Marmaro LLP

(57) ABSTRACT

A device and related method of use are disclosed which employ electrically-conductive wheels to massage and contact the skin to deliver electrical current. The present invention has both cosmetic and drug applications. In a cosmetic application, the rolling action of the wheels provides a light pressure skin massage that is important to reduce the appearance of skin surface irregularities. In a drug application, the device may be used to deliver ingredients of a conductive gel to or into the skin.

21 Claims, 5 Drawing Sheets

POWERED STIMULATION DEVICE

FIELD OF THE INVENTION

The present invention is directed to the field of providing electrical stimulation and massage to the body.

BACKGROUND OF THE INVENTION

The effects of age and excess weight gain on the body are well known. Gravity, sunlight, and other factors cause the skin to sag and the muscles to weaken as the body ages. The accumulation of fat cells in adipose tissue can result in unsightly bumps. These effects can be countered in part by massage, which causes a rearrangement of fatty deposits through external stimulation, and exercise, which keeps the skin firm and tight and the underlying muscles strong. Massage and exercise not only lead to a much-desired youthful appearance, but also improve the general health and physical wellbeing. The benefits of massage and exercise are widely appreciated.

Muscles are commonly exercised by physical exertion. This has many well-known mental and physical benefits. For example, the release of endorphins associated with exercise and exertion is known to have a positive effect on the brain. However, physical exertion is not always a possible, convenient, or safe means of exercising the muscles. For instance, physical activity associated with exercise can lead to stress on the joints and bones. This is especially problematic for the overweight, whose bones are subjected to greater stresses. The increased heart rate that accompanies physical exertion can be unhealthy for those with heart conditions or other impairments. Targeting and strengthening specific muscle groups that are not directly implicated in the movement of the limbs can also be difficult.

Muscles can also be exercised by electrical current stimulation, in much the same way the brain sends electrical stimuli to cause contraction of muscle cells. Electrical stimulation has the benefit of exercising muscles without requiring physical exertion, has found application in particular in passive exercising and in the re-education of atrophied muscle tissue. Electrical stimulation allows specific muscle groups to be targeted and exercised, and can be a safer alternative for those with medical conditions that do not allow for vigorous physical exertion. Electrical current can also improve local skin circulation and assist with local lymphatic drainage.

One method of stimulating muscles with electrical current has been the application of patches containing electrodes to the skin. Because patches are affixed to the skin and are generally only a few square inches or less in area, they suffer from the disadvantage that only a localized surface area of the skin can be stimulated at any given time. Patches may also cause skin irritation as discussed in more detail below.

Another way to firm the skin and muscles is through massage. Massage can stimulate muscle cells and redistribute the adipose tissue cells underlying the skin's surface. Rollers provide an ideal method of massage that can cover large surface areas with ease. Light pressure skin massage using rollers can also assist in the breakdown of skin surface irregularities. Massage with rollers thereby leads to smoother and more youthful-looking skin.

To date, massage and electrical stimulation have been viewed as separate activities requiring separate periods of treatment and separate specialized equipment. This leads to greater expense and inconvenience for those wishing to enjoy the benefits of both electrical stimulation and massage. Electrical stimulation of multiple muscle groups by patches leads to the greater inconvenience of having to continually place and remove patches.

There is therefore a need for a single device that combines the therapeutic effects of electric stimulation and roller massage.

SUMMARY OF THE INVENTION

One object of the present invention is to combine the therapeutic effects of electric stimulation and roller massage in a single device. Another object of the present invention is to effectively deliver electric current concurrently with massage of the skin. Another object of the present invention is to deliver electric current to a large surface area of the skin. Other objects of the invention are to improve the appearance of the skin and to deliver ingredients to or into the skin. Other uses of the present invention may be apparent to one skilled in the art. In describing this invention, the term "user" refers to the person delivering the massage and the term "subject" refers to the person receiving the massage (which may be the same as the user).

One embodiment of the present invention provides an apparatus for stimulating therapy which is comprised of one or more stimulating knobbed wheels arranged in parallel relationship with each other. The stimulating assembly is pressed onto a human skin and underlying tissues and rolled in the forward and backward directions, thereby applying the stimulation to the skin and underlying tissues. Concurrently with the rolling motion, electrical current is delivered from the stimulating assembly to or into the skin and underlying tissues by means of one or more electrically-conductive wheels. Thus, a superior stimulating effect can be achieved that combines the benefits of both massage and electrical stimulation.

The device may be used with a conductive gel to more effectively deliver the current to or into the skin. The conductive gel is applied to the skin in the areas of treatment and provides improved conductivity between the electrodes and the skin. The conductive gel may be water soluble and may have firming and tightening agents that improve the appearance of the skin. The gel may be wiped off the skin following the use of the device, leaving the skin with a clean and improved-looking appearance. Thus, the gel can be used as part of the treatment to augment the results obtained from the application of the device.

In general, electrical stimulation devices can be characterized as bipolar or monopolar, though devices may also be multipolar. Whether a device is monopolar or bipolar will in part define its physical appearance and design. Both bipolar and monopolar devices have two electrodes, but in bipolar devices the electrodes are situated close together whereas in monopolar devices a primary electrode delivers the electric current at a delivery site and a secondary electrode may be situated anywhere else on the body. In one embodiment of the invention, the electrodes are situated close together in a bipolar configuration, the wheels providing both electrodes. However, the invention can also be configured in a monopolar fashion, with one electrode providing the stimulation and the other electrode being applied to some other part of the body.

The present invention contains a number of benefits over the prior art. In contrast to the. limited area of stimulation provided by patches, wheels can apply stimulation over a relatively wide surface area of the skin. In one embodiment, the device can roll over portions of the body having substantially large surface areas such as the back, legs, arms, or torso. In another embodiment, the device may be small enough to roll over the surface contours of the face, hands, or other smaller areas of the body to stimulate localized skin surface areas that would be difficult or impossible to target with conventional electric current delivery methods. Thus, the present invention is adaptable to treat and stimulate variously-sized surface areas in the body. This effect is not limited to any localized area of the skin, but can be delivered to arbitrarily large surface areas without the need to reconfigure or adjust the mechanical or electrical components of the device.

Another benefit of the present invention is the ability to operate at variable non-linear voltage or current levels. Electric current can be controlled either by varying the voltage or by varying the current. Delivery of electric current to or into the skin is affected by the skin's resistance or impedance level, which may vary over time based on any number of factors such as moisture content of the skin, temperature, skin type, pressure at which the massage is carried out, or duration and intensity of treatment. Varying the voltage or current can provide a more uniform treatment effect that compensates for changes in the impedance or resistance level of the skin over time and among different subjects.

In one embodiment of the invention, a knob is provided to vary the voltage level, thereby providing voltage-control. Voltage-control has the benefit of being less expensive to implement than current-control, and is suitable for non-critical applications such as the topical delivery of electric current to or into the skin. In voltage control embodiments, the current will automatically adjust to the selected level of voltage.

In other embodiments, it may be preferable to adjust the current rather than voltage, and thereby provide current control. In the case of current control, the voltage will automatically adjust to the selected level of current. Current control maybe preferable in some embodiments because it is the current, rather than the voltage, that provides the stimulating effect on the skin and muscles. Thus, controlling the current level provides for an accurate and precise means of delivering the stimulation and accounting for fluctuations in factors such as skin impedance or resistance. This is especially important when providing stimulation to sensitive organs or muscles within the body.

In traditional electrical stimulation devices, current and voltage adjust automatically according to the well-known Ohm's law, expressed as V=IR. As this law suggests, there is a linear relationship between voltage and current in traditional devices. That is, as voltage increases, current increases in proportion to the resistance provided by the circuit. The present invention is unique compared to traditional devices in providing at least a partial non-linear electrical flow whereby the current and voltage are capped at certain preset levels. This non-linear relationship is embodied in the internal electronics of the device, thereby providing greater safety in the occasion of a short-circuit or malfunction, that is, because the relationship is partially or wholly non-linear, a sudden decrease in resistance will not cause a spike in voltage or current. This protects the subject against injury and prevents damage to the internal circuit components.

Because the electrical current or voltage is variable, it is possible to select a suitable electrical current to apply optimum stimulation, depending upon the particular needs and comfort level of the subject and the muscle group to be stimulated. The current or voltage delivery is adjustable with a simple turn dial on the device.

In one embodiment, another advantage of the present invention is provided by the knobbed or other non-flat surface configuration of the wheels. The skin has a normal layer of dry surface cells that protects the skin, but lowers conductivity and increases the skin's resistance or impedance. A knobbed or other non-flat surface is better able to conduct electricity through this layer of dry skin cells to the more conductive skin cells underneath.

In contrast, the flat electrodes in the prior art experience lower conductivity at the skin-electrode interface. When used in combination with the conductive gel, conductivity may be increased even further by providing better contact with the underlying skin cells. By improving conductivity, the same stimulating effect can be achieved with lower voltage levels, providing for a smaller, simpler, more efficient and safer device.

Another advantage of the present invention is that monophasic current may be used to stimulate the skin. Monophasic current has the advantage of requiring less current to obtain the desired stimulation effect. Thus, devices using monophasic current can be powered for a longer period of time by compact portable batteries and therefore be manufactured to have smaller dimensions and lower weight. Monophasic current can also be created using cheaper and simpler components. This lowers the cost of the device by lowering the cost of its component parts and simplifying the manufacturing process. In other embodiments, biphasic current may be used.

The present invention has both cosmetic and drug applications. In a cosmetic application, the rolling action of the wheels provides a direct topical skin massage that when combined with electrical stimulation, is effective to improve the appearance of the skin and its surface irregularities.

The present invention has a drug application as well. Generally speaking, surface skin irregularities can be caused by the accumulation of fat cells and the presence of excessive superficial cutaneous tissue fibers. For example, a primary reason for surface skin irregularities is the dimpling effect caused by accumulation of fat cells between the dermis and underlying connective tissue, primarily in the hips-thighs-buttocks region of the human body. Skin irregularities and the "orange peel" appearance of skin are due to organization of fat cells and the presence of connective tissue in the superficial dermis.

In one aspect of the drug application, the present invention improves the appearance of the skin by improving superficial skin blood circulation. Greater blood flow corresponds to greater oxygen delivery to the site, leading to healthier looking skin. Combining massage and electrical stimulation in one effective treatment improves the appearance of skin and selectively improves muscle tone in the areas of use.

In another aspect of the drug application, the present invention relates to the facilitating ionic transfer to or into the skin by monophasic current. Electricity interacts with the skin in a well-known electrochemical process by increasing or decreasing the flow of ions through the skin. Monophasic current operates to increase the flow of ions in one direction only, that is, either "pulling" ions away from the skin or "pushing" ions towards the skin. Biphasic current operates to cause ion flow in both directions by alternating between "pulling" and "pushing."

In another aspect of the drug application, the present invention can be used with either monophasic or biphasic current. In one embodiment, monophasic current is used to facilitate ionic transfer to or into the skin. Monophasic current has not traditionally been employed in electrical stimulation devices due to increased risk of skin irritation. When combined with rolling massage, the risk of skin irritation is substantially reduced because the current is not focused on one particular patch of skin.

In another aspect of the drug application, the present invention may be used as an adjunct for delivery of the gel's active ingredients to or into the skin. The gel may be configured to contain a solution of charged (ionized) particles. When used in conjunction with monophasic current provided by the device's electrodes, the electric field will "push" the charged particles to or into the skin, thereby creating a means for delivering ingredients to or into the skin by electric current.

For example, in a simple salt water solution, polar water molecules divide the salt molecule into positively-charged sodium ions ($Na^+$) and negatively-charged chloride ions ($Cl^-$). Depending on the direction of electric flow, monophasic electric current can be applied to drive either the sodium or chloride ions into the skin. Using this technique, it is possible to drive many ionic gel solvents into the skin.

In an additional embodiment of the present invention, the electrodes may vibrate to provide further stimulation to the skin and underlying tissues. Vibration may be provided by means of pads or other non-rolling electrodes. The electrodes may be contained on a single vibrating pad, or may be contained on separate pads.

DETAILED DESCRIPTION

Figure 1:
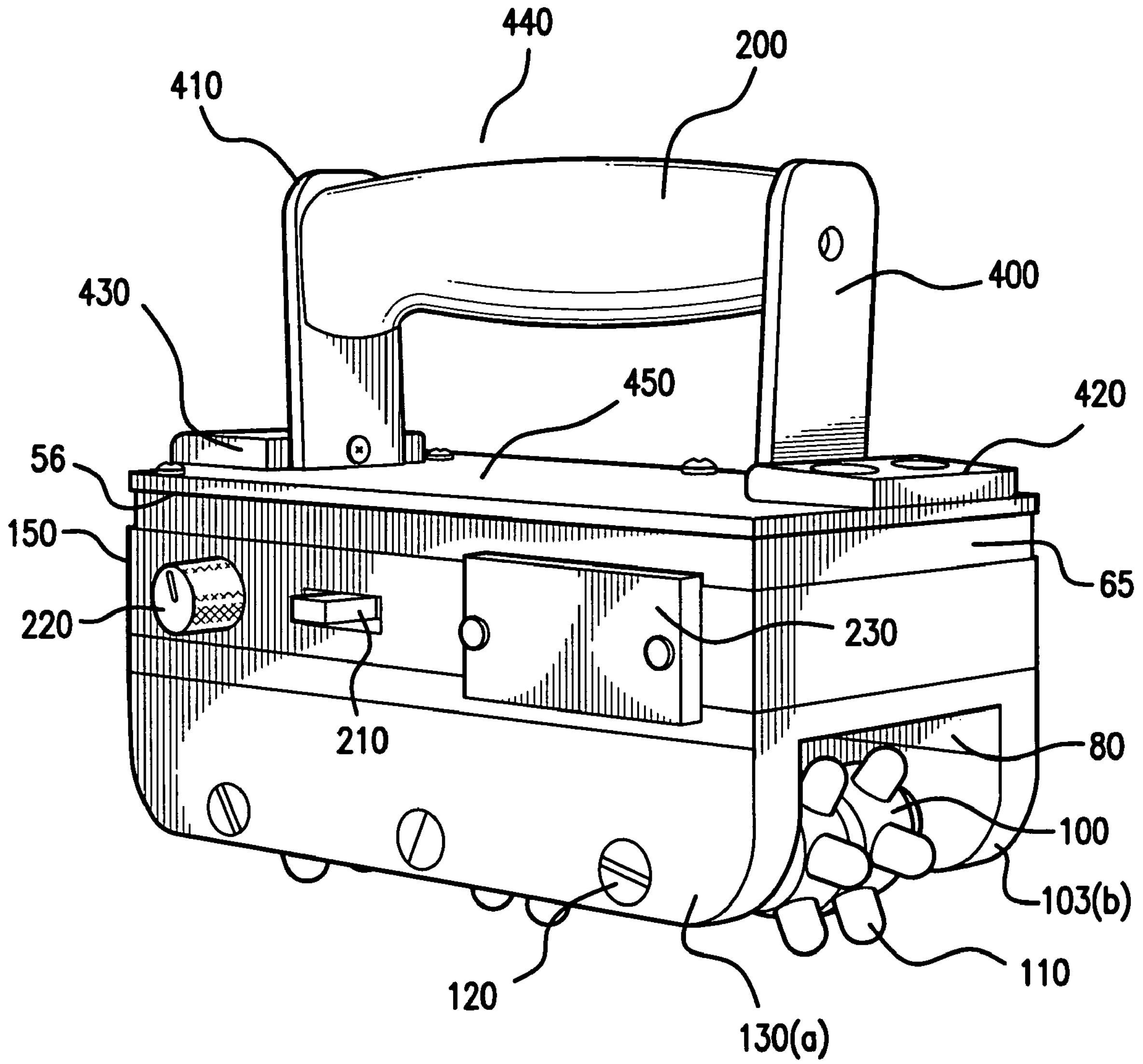
FIG. 1 shows a perspective view of an embodiment of the device.

A perspective view of one embodiment of the device or apparatus of the present invention is shown in FIG. 1. As shown in FIG. 1, the apparatus has a generally rectangular housing 150 with an upper surface 450, two longer sides 55 (not shown) and 60 comprising the longer sides of the rectangular housing, and two shorter sides 65 and 70 (not shown) at the front and back comprising the shorter sides of the rectangular housing. Secured to the upper surface 450 is a handle assembly 440 capable of holding the device securely when in use or when being transported. The handle assembly extends along the longer sides of the housing to provide leverage when the device is put into motion in a longitudinal direction. The handle assembly is comprised of a grip 200, a first support 410, a second support 400, and fastening plates 420 and 430.

The grip 200 may be composed of a cushioning material to absorb shocks caused by the rolling motion of the device as it is used over the contours of the body, and to provide for comfort when in use. Fastening means secure the grip in place by coupling its longitudinal ends to the first support 410 and the second support 400. The first and second supports extend in a downward direction from the grip towards the upper surface 450 such that together with the grip, they form an inverted u-shape to allow the user's fingers to comfortably and securely wrap around the grip. Fastening plates 420 and 430 are coupled, on the hone hand, to the upper surface 450, and on the other, to the first and second supports by screws or other fastening means.

As shown in the diagrams, each of the longer sides 55, 60 is generally vertically disposed, such that an upper edge 56, 61 of the longer sides 55, 60, respectively, is disposed adjacent the upper surface 450. Each of the longer sides 55, 60 includes a lower portion 130*a*, 130*b*, respectively. The lower portions 130*a* and 130*b*, in turn, define therebetween an internal cavity 80. The corners of the lower portions may be curved in order to be blunt rather than sharp, so as to provide comfort and safety when in use. Situated in the cavity 80 are a plurality of wheels 100 and axles 120. Each axle has one or more wheels joined thereto in a rotatable configuration. Portions of each wheel extend beyond the lower portions 130*a*, 130*b* such that the wheels may contact a surface without substantial physical interference from the lower portions. The internal cavity 80 is of sufficient depth to allow the wheels to rotate about the axles without substantial physical interference. Provided on the external surface of the rectangular housing are a dial 220, a power switch 210, and a battery cover 230 which are described in more detail below with reference to FIG. 2.

Figure 2:
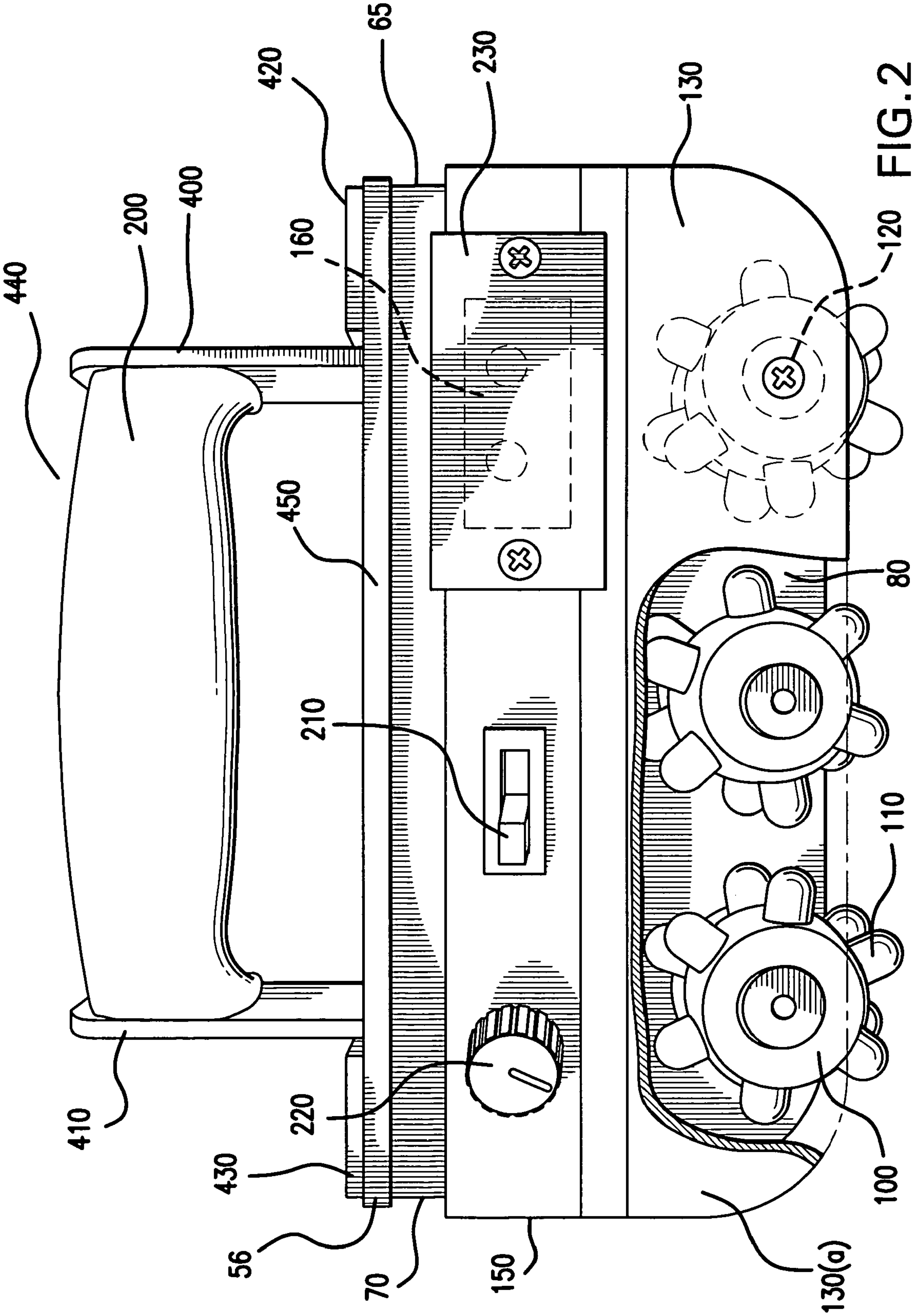
FIG. 2 shows a left side view of the embodiment of FIG. 1.

A left side view of the device with a cutaway view of the wheels is shown in FIG. 2. A power switch 210 is used to turn the electrical current on and off, and a dial 220 allows the electrical current or voltage to be varied. In the embodiment depicted in the figures, the electrical current is to provide stimulation to the muscles, however in other embodiments it may have the additional function of providing power to drive the wheels. The electrical current may be supplied by batteries 160, which may be held within an upper portion of the device by a removable battery cover 230.

Figure 3:
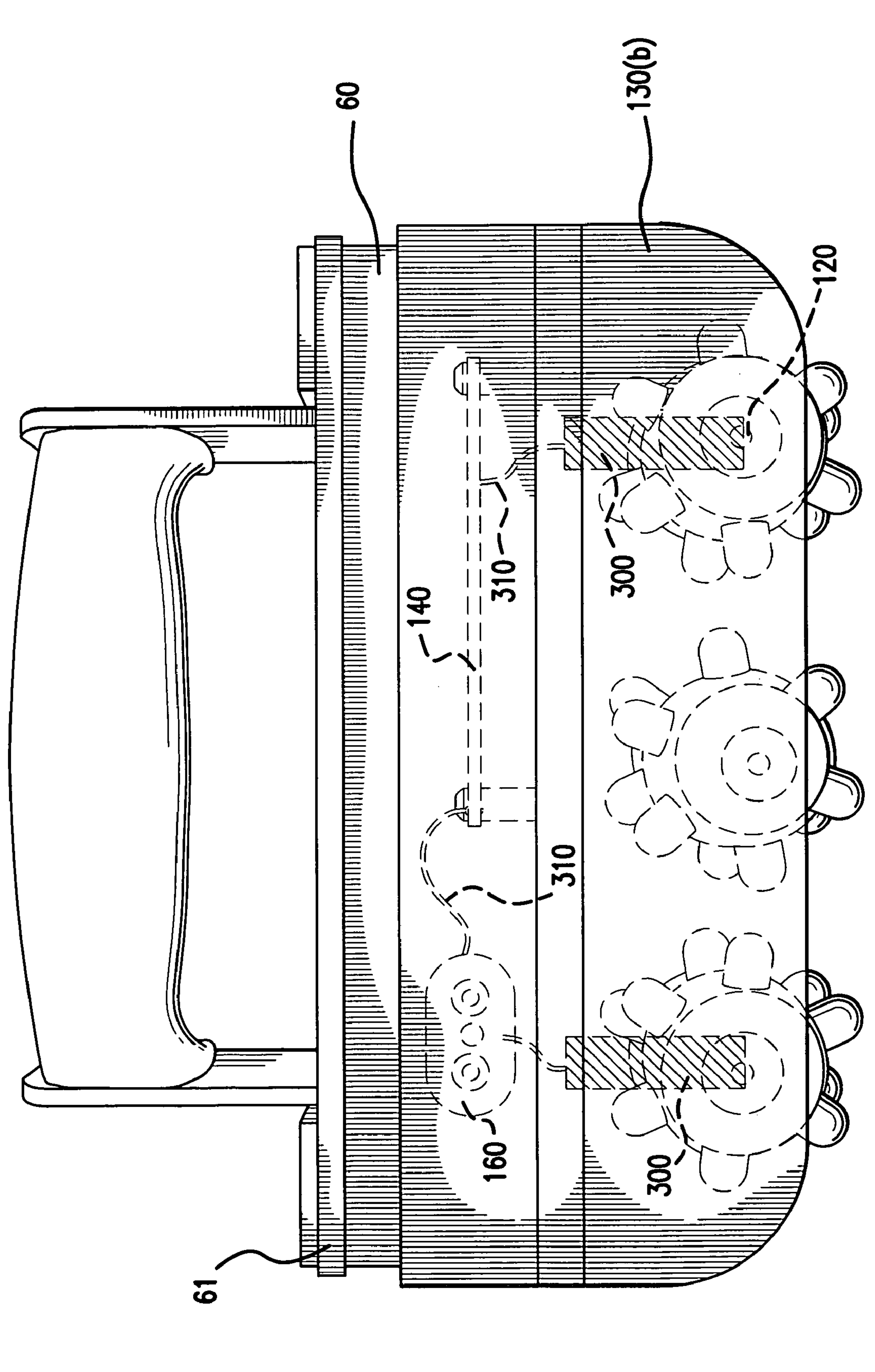
FIG. 3 shows a right side view of the embodiment of FIG. 1.

FIG. 3 shows a right side view of the device with the batteries 160, circuit board 140, and conductive strips 300 shown in phantom and connected together via wires 310. A spacer 170 is positioned between each wheel, and between the wheel and the lower portion 130*a* or 130*b*. The conductive strips conduct electrical current to the axles 120 through contact with the spacers 170, which, in turn, conduct the electrical current to the wheels 100, thereby forming an electric circuit. Electrical current is conducted between the conductive strips 300 and the wheels by means of physical contact between the conductive strips 300, spacers 170 (see, e.g., FIG. 2), and the wheels 100. In particular, as shown in FIG. 3, the wires conduct electrical current between the batteries 160 and the circuit board 140, the batteries 160 and one conductive strip 300, and between the circuit board 140 and another conductive strip 300. The conductive strips, in turn, conduct electrical current to the spacers 170 by means of physical contact with the spacers. Depending on the friction between the spacers and the wheels, the spacers may or may not rotate about the axles as each wheel is turned.

The conductive strips thereby provide conductivity between the moving parts of the device, which include the wheels, and the non-moving parts of the device, which include the balance of the device's component parts, including the axles and the circuit board. As shown in FIG. 3, the device may contain three axles with wheels, but the two endmost axles with wheels are provided with electrical current. This allows a circuit to be formed between the two endmost axles. In this arrangement, it is important that the material composition of the wheels, axles, and other parts of the circuit to which electricity is provided is conductive in nature. For example, the wheels may be made in part of steel or aluminum, but not wholly of a non-conductive plastic or ceramic. Moreover, the composition of the wheel need not be uniform, and may have both non-conductive parts and conductive parts, as long as conductive portions come into contact with the skin. For the middle axle and set of wheels, since no electrical current is being provided, the conductivity of the material composition is not important. Therefore, these components may be made of any material without regard to conductivity.

Figure 4:
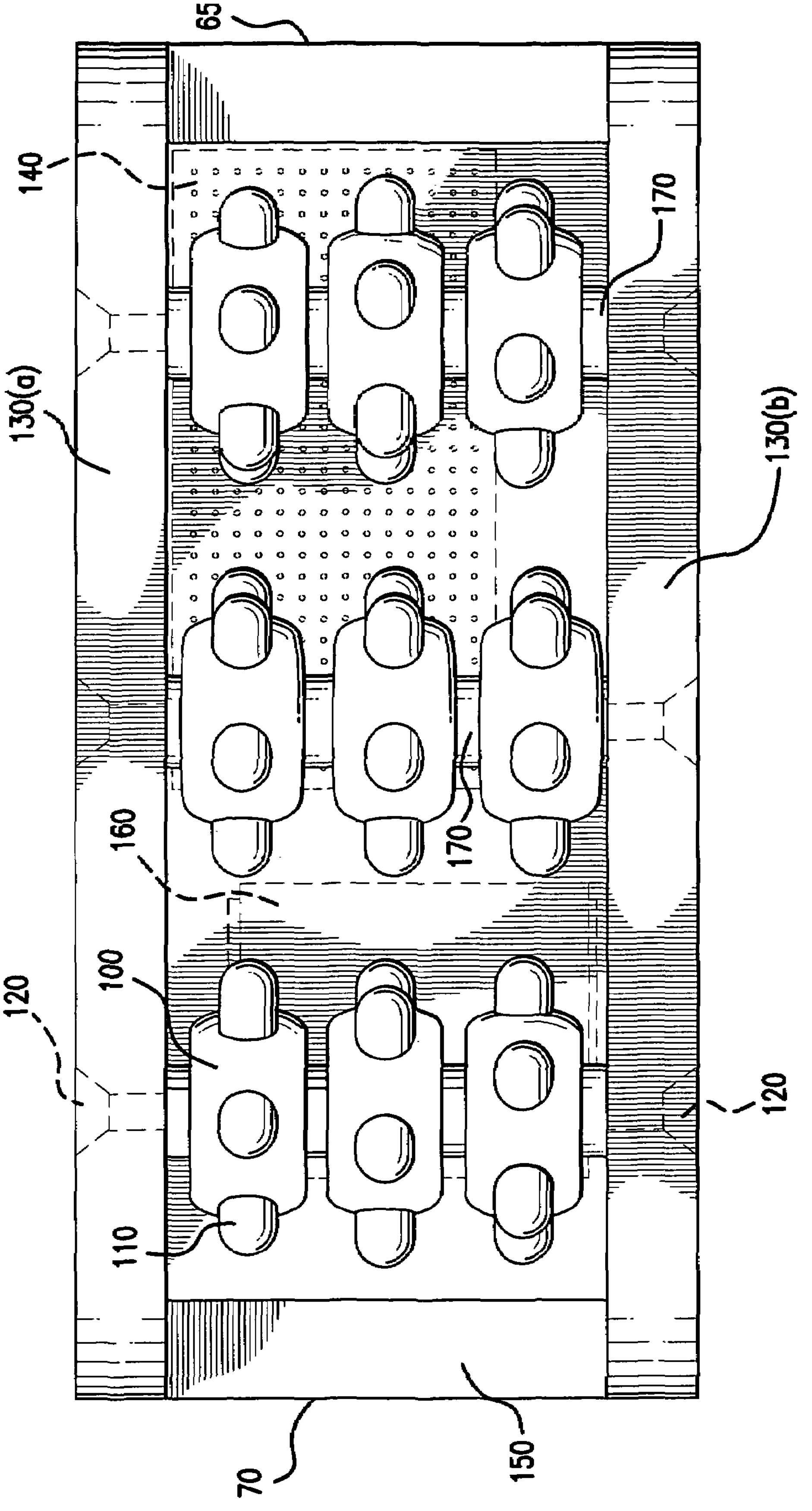
FIG. 4 shows a front view of the embodiment of FIG. 1.

With reference to the bottom view shown in FIG. 4, the massage device contains a housing 150 having a lower portions 130*a* and 130*b* that supports the axles 120. Wheels 100 are pivotally mounted on the axles such that the wheels may rotate freely. Wheels 100 are separated by spacers 170 that hold the wheels apart and secure them from moving laterally along the length of the axles.

The wheels may have knobs 110 for massaging the skin. When provided, knobs 110 have the benefits described above, including the ability to penetrate the dry layers of skin to better conduct electricity, the exertion of greater pinpoint pressure to massage and stimulate the muscles, breaking down surface irregularities, and improving the appearance of the skin.

In other embodiments, however, knobs may not be not present. For example, in smaller devices that target the face, knobs could impede free rotation of smaller-diameter wheels. In other embodiments, a smooth and flat rolling surface may be desirable for comfort or other reasons, such as where conductivity and high pressure massage are less of a concern.

In yet other embodiments, the wheels 100 may be driven by a motor such that the movement of the wheels causes the entire device to be self-propelled in forward or backward directions across the body. Thus, the device may be put into use with less effort as it does not require external force to be put into motion. Driving of the wheels may be accomplished by means of a belt, chain, wheel and pulley system, or by any other means apparent to one skilled in the art. Engagement of the drive mechanism can be provided by a switch, knob, or other input mechanism, and may further provide for switching between driving in the forward or backwards directions. Knobs on the wheels may have further use in this embodiment by providing traction in much the same way knobbed treads on tires may provide traction to the driven wheels of a motor vehicle.

Figure 5:
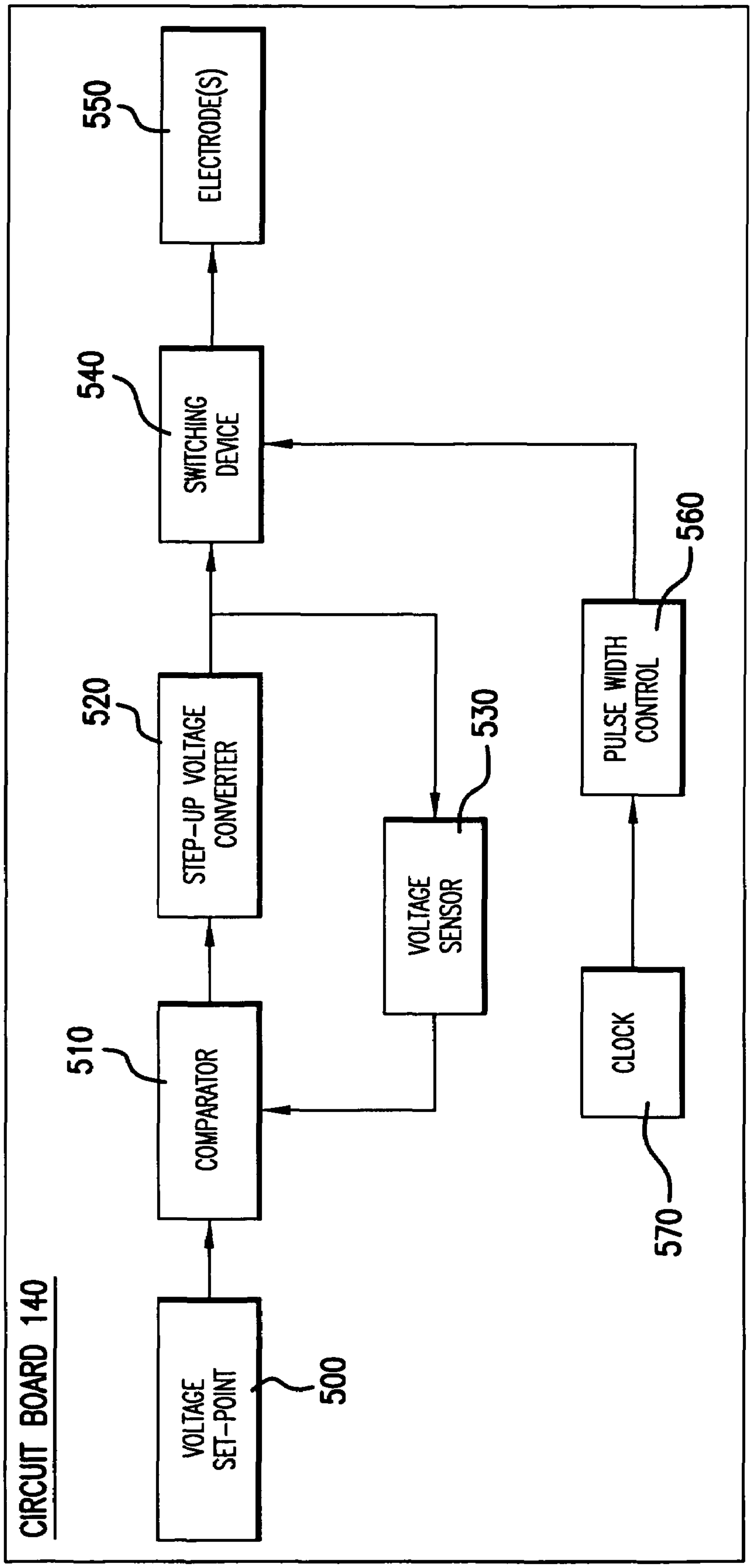
FIG. 5 shows a high-level schematic of the electronics employed in an embodiment of the present invention.

As shown in FIG. 3, a circuit board 140 powered by batteries 160 is contained within the rectangular housing 150 and produces an electric current which is delivered through the axles 120 to one or more of the wheels 100. FIG. 5 shows a high-level functional schematic of the electronic components of the circuit board 140. These components make it possible to deliver an electric current strong enough to provide stimulation with small portable batteries. For example, in one embodiment, the electrical circuit is powered by two small "AA" size batteries that deliver 1.5 volts each. The batteries may be combined either in series or in parallel to deliver a sufficiently strong voltage to drive an output current, which, in turn, triggers an action potential in targeted nerve or muscle cells and thereby causes the desired stimulating effect. Small "AA" size batteries are also low in cost, widely available, and can be replaced or recharged with ease.

In one embodiment, the circuit board 140 is comprised of a variety of components. A voltage set point 500 and voltage sensor 530 are provided as input to a comparator 510. In the voltage set point 500, the voltage is set by means of precision resistors (1%) and a variable resistor arranged in a voltage divider configuration. The resistance at the variable resistor is adjusted to change the voltage set-point. In the voltage sensor 530, the output node of a step-up voltage converter 520 is down converted through the voltage divider of the voltage set-point. The center node of this voltage divider is fed into one of the two terminals of a high-input impedance comparator 510. The other terminal of the comparator 510 is fed with an ultra-precise fixed reference voltage. In the comparator 510, a two terminal, fast high-input impedance comparator compares the set-point voltage, by means of the voltage sensor 530, with the ultra-precise fixed reference voltage. If the ultra-precise fixed reference voltage is higher that the voltage at the other terminal of the comparator, then the comparator 510 signals the step-up voltage converter 520 to increase the voltage.

The output of the comparator 510 is fed into a step-up voltage converter 520 which outputs to a switching device 540. The step-up voltage converter 520 is an inductive charge pump that is turned on and off by the comparator 510. When the charge pump is on, the inductive component of the step-up voltage converter 520 is forced to oscillate, thus continuously increasing the voltage at its output node. The switching device 540 is a low-threshold field-effect transistor. The voltage at the gate of the transistor is controlled by a voltage pulse sent by a pulse-width control unit 560. When this pulse is present, the gate of the transistor is polarized, thereby allowing current to flow between the electrode(s) 550 and a reference, which could be an electrode itself.

A clock 570 provides output to the pulse-width control unit 560 that controls the width of the electrical pulses that are delivered to the electrodes 550. The clock 570 is a multivibrator configured as an astable with both frequency and duty cycle fixed, though in other embodiments the frequency and duty cycle can be variable. The pulse-width control unit 560 is a multivibrator configured as a monostable with a fixed-pulse or variable-pulse duration. This monostable configuration is triggered by the clock. The pulse-width control unit drives the voltage at the gate of the transistor in the switching device. The switching device 540 combines the output voltage from the step-up voltage converter 520 with the output of the pulse width control unit 560 to provide the final output current that is delivered to the electrode(s) 550. The electrode (s) 550 constitute the contact point with the body.

In one embodiment of the invention, the electric circuit delivers square pulses at 60 Hz. The voltage is in the range of 14-148 volts, plus or minus 10 volts, with voltage control provided. Current in the voltage control circuit will automatically adjust to the selected voltage level. In other embodiments, providing current control will be more desirable because current drives the stimulation effect. In either form of control, current or voltage will not exceed a certain preset level due to protective measures built into the circuitry.

To facilitate the flow of electrical current, the muscle stimulator device may be used with a conductive gel applied to the skin in the areas of treatment. The conductive gel may be water soluble and may have firming and tightening agents that improve the appearance of the skin. The gel may be wiped off the skin following the use of the device. The gel can be used as part of the treatment to augment the results obtained from the device.

In an additional embodiment of the present invention (not depicted), the electrodes may vibrate to provide further stimulation to the skin and underlying tissues. Vibration may be provided by means of pads or other non-rolling electrodes. The electrodes may be contained on a single vibrating pad, or may be contained on separate pads. If contained on a single pad, the electrical current flows from an electrode on the pad through the skin to another electrode on the same pad. If electrodes are contained on separate pads, the electrical current flows from an electrode on one pad through the skin to a separate electrode on a separate pad.

The electrodes may comprise all or a portion of the contact surface of the vibrating pad. A vibrating pad must be of sufficient surface area to have the desired effect. An electrode can typically deliver a current with a relatively smaller surface area than that required to have the desired effect. Thus, the electrode may comprise a smaller surface area than the contact surface of the vibrating pad.

Alternately to providing vibration by means of a pad, vibration may be provided by rolling electrodes substantially as described above. In this instance, an additional vibrating mechanism is provided to vibrate the wheels, as is well known in the art. The addition of vibration to the present invention provides, in addition to electrical stimulation and massage, another means of stimulating the skin and underlying muscles in accordance with the various aspects and applications of the invention as described herein.

Without departing from the spirit and scope of this invention, one of ordinary skill in the art can make various changes and modifications to the present invention to adapt it to various uses and conditions. As such, these changes and modifications properly fall within the scope of the invention.

The invention claimed is:

1. A muscle stimulator device, comprising:

a non-conductive housing having opposing sides, said sides defining depending lower portions;

first and second axles each joined in a perpendicular configuration to said opposing lower portions; and at least one wheel joined to the first axle in a rotatable configuration, the wheel readily massaging portions of the human body when brought into contact therewith, at least one wheel joined to the second axle in a rotatable configuration, the wheel readily massaging portions of the human body when brought into contact therewith, wherein the wheels of the first and second axles each comprise at least one electrode for delivering electrical current to the muscles, an electrical circuit contained within the housing configured to selectively generate and deliver to the electrodes an electrical current for providing a stimulating effect to the muscles, wherein the electrical circuit extends along the first and second axles from one depending lower portion to the other depending lower portion, wherein the electrical circuit is formed between the first and second axles, whereby electrical current is delivered to the muscles along the entire area between the at least one electrode on the first axle and the at least one electrode on the second axle when the electrodes are placed in contact with a portion of the human body; and said device includes a third axle positioned between the first and second axles, at least one wheel joined to the third axle in a rotatable configuration, wherein the third axle is not part of the electrical circuit.

2. The device of claim 1, wherein the housing is generally rectangular and has an upper surface, two longer sides, two shorter sides, and wherein a handle assembly is disposed on the upper surface for securely gripping the device.

3. The device of claim 2, wherein the handle assembly is comprised of a grip, first support, and second support, wherein the first and second supports extend from the grip to the upper surface, forming an inverted U-shape such that a user's fingers may comfortably and securely wrap around the grip.

4. The device of claim 1, further comprising a power source, a circuit board and two pairs of conductive strips that are electrically connected to the circuit board, wherein one pair of conductive strips are associated with the first axle and the other pair of conductive strips are associated with the second axle, thereby delivering electrical current to the electrodes.

5. The device of claim 1, wherein each one of the axles includes a plurality of wheels mounted thereon.

6. The device of claim 5, wherein a spacer is mounted between each of the wheels on an axle, the spacer being configured to prevent lateral movement of the wheels along the axle.

7. The device of claim 1, wherein a spacers are mounted on said first and second axles on each side of the wheels, the spacers being configured to prevent lateral movement of the wheels along the axles, and wherein the spacers are electrically connected to the wheels.

8. The device of claim 1, wherein the lower portions include corners, and wherein the corners of the lower portions are curved to provide a blunted contour that reduces the probability of scratches or other injuries caused by massaging portions of the human body when brought into contact therewith.

9. The device of claim 1, wherein the electrical circuit delivers monophasic electrical current.

10. The device of claim 1, wherein the electrical current is configured to provide a range of selectable voltages and an automatically-adjusting current level that is automatically determined according to a selected voltage level.

11. The device of claim 1, wherein the electrical current is configured to provide a range of selectable current levels and an automatically adjusting voltage level that is automatically determined according to a selected current level.

12. The device of claim 1, wherein the circuit is configured such that at a plurality of voltage levels, a non-linear relationship exists between the voltage and current levels of the electrical current.

13. The device of claim 1, wherein the circuit is configured such that at a plurality of voltage levels, a linear relationship exists between the voltage and current levels of the electrical current.

14. The device of claim 1, wherein the electrical circuit delivers biphasic electrical current.

15. The device of claim 1, wherein the wheel is provided with a plurality of massaging knobs around the perimeter of the wheel.

16. The device of claim 1, wherein the wheel is driven by an electrical current.

17. A muscle stimulator device, comprising:

a generally rectangular non-conductive housing having an upper surface, two longer sides, and two shorter sides, wherein a battery cover, power switch, and electrical adjustment dial is provided on one or more of the longer sides;

two depending opposing lower portions having curved corners, the lower portions extending along the length of each of the longer sides of the rectangular housing opposite the upper surface;

a circuit board disposed within the rectangular housing and electrically connected to one or more batteries, the circuit board generating a monophasic electrical current;

at least two axles extending across the cavity, each axle having two ends, each end joined to an opposing lower portion;

a plurality of wheels joined to each of the axles in a rotatable configuration, the wheels having a plurality of knobs spaced at equal distances around the wheel's perimeter, where a portion of the wheels including their knobs are external to the lower portions such that the wheels may readily massage portions of the human body when brought into contact therewith;

spacers positioned on the axles outside of the wheels and between the wheels that prevents lateral movement of the wheels along the axles;

first and second pairs of conductive strips electrically connected to the circuit board, and making electrical contact with the outermost spacers on each end of the axles, wherein the electric current is delivered from the circuit board through the conductive strips and through the spacers to the wheels forming an electrical circuit, and wherein the electrical circuit is formed between the first and second axles, whereby electrical current is delivered to the muscles along the entire area between the electrodes on the first axle and the electrodes on the second axle when the electrodes are placed in contact with a portion of the human body; and said device includes a third axle positioned between the first and second axles, at least one wheel joined to the third axle in a rotatable configuration, wherein the third axle is not part of the electrical circuit.

18. A method for muscle stimulation, comprising:

providing a device having:

a non-conductive housing having opposing sides, said sides defining depending lower portions;

first and second axles each joined in a perpendicular configuration to said opposing lower portions; and at least one wheel joined to the first axle in a rotatable configuration, the wheel readily massaging portions of the human body when brought into contact therewith, at least one wheel joined to the second axle in a rotatable configuration, the wheel readily massaging portions of the human body when brought into contact therewith, wherein the wheels of the first and second axles each comprise at least one electrode for delivering electrical current to the muscles, an electrical circuit contained within the housing configured to selectively generate and deliver to the electrodes an electrical current for providing a stimulating effect to the muscles, wherein the electrical circuit extends along the first and second axles from one depending lower portion to the other depending lower portion, wherein the electrical circuit is formed between the first and second axles; and said device includes a third axle positioned between the first and second axles, at least one wheel joined to the third axle in a rotatable configuration, wherein the third axle is not part of the electrical circuit;

providing electrical current to the wheels such that when contacting the skin, an electrical circuit is formed between the first and second axles; and massaging the skin with the wheel while simultaneously providing the electrical current to the wheels, whereby electrical current is delivered to the skin along the entire area between the at least one electrode on the first axle and the at least one electrode on the second axle.

19. A muscle stimulator device, comprising:

a non-conductive housing having opposing sides;

a vibration generating means joined to the housing;

first and second vibrating members joined to the vibration generating means and readily massaging portions of the human body when brought into contact therewith, wherein the first and second vibrating members are spaced apart, wherein the first and second vibrating members each comprise at least one electrode for delivering electrical current to the muscles, an electrical circuit contained within the housing configured to selectively generate and deliver to the electrodes an electrical current for providing a stimulating effect to the muscles, wherein the electrical circuit is formed between the first and second vibrating members, whereby electrical current is delivered to the muscles along the entire area between the at least one electrode on the first vibrating member and the at least one electrode on the second vibrating member when the electrodes are placed in contact with a portion of the human body; and said device includes a third axle positioned between the first and second axles, at least one wheel joined to the third axle in a rotatable configuration, wherein the third axle is not part of the electrical circuit.

20. A muscle stimulator device, comprising:

a non-conductive housing having opposing sides, said sides defining depending lower portions;

first and second axles each joined in a perpendicular configuration to said opposing lower portions;

a vibration generating means joined to the housing;

at least one wheel joined to the first axle in a rotatable configuration, the wheel both providing vibration from the vibration generating means and readily massaging portions of the human body when brought into contact therewith, at least one wheel joined to the second axle in a rotatable configuration, the wheel both providing vibration from the vibration generating means and readily massaging portions of the human body when brought into contact therewith, wherein the wheels of the first and second axles each comprises at least one electrode for delivering electrical current to the muscles, an electrical circuit contained within the housing configured to selectively generate and deliver to the electrodes an electrical current for providing a stimulating effect to the muscles, wherein the electrical circuit extends along the first and second axles from one depending lower portion to the other depending lower portion, wherein the electrical circuit is formed between the first and second axles, whereby electrical current is delivered to the muscles along the entire area between the at least one electrode on the first axle and the at least one electrode on the second axle when the electrodes are placed in contact with a portion of the human body; and said device includes a third axle positioned between the first and second axles, at least one wheel joined to the third axle in a rotatable configuration, wherein the third axle is not part of the electrical circuit.

21. A muscle stimulator device, comprising:

a non-conductive housing having opposing sides, the sides defining depending lower portions, wherein the housing is generally rectangular and has an upper surface, two longer sides, two shorter sides, and wherein a handle assembly is disposed on the upper surface for securely gripping the device, first, second and third axles each joined in a perpendicular configuration to the opposing lower portions, wherein the third axle is located between the first and second axles, wherein each of the axles include a plurality of wheels mounted thereon in a rotatable configuration, wherein each of the wheels on the first and second axles each comprise at least one electrode for delivering electrical current to the muscles, wherein spacers are mounted on the first, second and third axles on each side of the wheels, the spacers being configured to prevent lateral movement of the wheels along the axles, a power source, a circuit board and first and second pairs of conductive strips that are electrically connected to the circuit board, wherein the first pair of conductive strips are connected to opposite ends of the first axle and the second pair of conductive strips are electrically connected to opposite ends of the second axle, an electrical circuit contained within the housing configured to selectively generate and deliver to the electrodes an electrical current for providing a stimulating effect to the muscles, wherein the electrical circuit extends along the first and second axles from one depending lower portion to the other depending lower portion, wherein the third axle is not part of the electrical circuit, and wherein the electrical circuit is formed between the first and second axles, whereby electrical current is delivered to the muscles along the entire area between the electrodes on the first axle and the electrodes on the second axle when the electrodes are placed in contact with a portion of the human body.

* * * * *